(12) United States Patent
Mitsuhashi et al.

(10) Patent No.: US 11,540,793 B2
(45) Date of Patent: Jan. 3, 2023

(54) X-RAY IMAGING SYSTEM

(71) Applicant: Shimadzu Corporation, Kyoto (JP)

(72) Inventors: Takayuki Mitsuhashi, Kyoto (JP); Haruo Uno, Kyoto (JP); Ken Shirota, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 222 days.

(21) Appl. No.: 17/150,180

(22) Filed: Jan. 15, 2021

(65) Prior Publication Data
US 2021/0378612 A1    Dec. 9, 2021

(30) Foreign Application Priority Data
Jan. 15, 2020   (JP) .............................. JP2020-004624

(51) Int. Cl.
*A61B 6/00*      (2006.01)
*H01J 35/10*     (2006.01)
*H05G 1/30*      (2006.01)

(52) U.S. Cl.
CPC .............. *A61B 6/4476* (2013.01); *A61B 6/54* (2013.01); *H01J 35/101* (2013.01); *H05G 1/30* (2013.01); *H01J 2235/1026* (2013.01)

(58) Field of Classification Search
CPC ........... A61B 6/00; A61B 6/4476; A61B 6/54; H01J 35/10; H01J 35/101; H01J 2235/1026; H05G 1/30; H05G 1/46; H05G 1/66
See application file for complete search history.

(56) References Cited

U.S. PATENT DOCUMENTS 9,820,705 B2 *   11/2017   Kim ..................... G03B 21/208

FOREIGN PATENT DOCUMENTS

JP         2014191935 A     10/2014

* cited by examiner

*Primary Examiner* — Jurie Yun
(74) *Attorney, Agent, or Firm* — Muir Patent Law, PLLC

(57) ABSTRACT

Provided is an X-ray imaging system capable of performing X-ray imaging quickly. The X-ray imaging system is provided with: an X-ray tube device including a cathode and an anode, the X-ray tube device being capable of performing X-ray imaging by irradiating an imaging target with X-rays in a state of rotating the anode; a light irradiation device including a collimator defining an X-ray irradiation range of the X-rays with respect to the imaging target, a visible light irradiation unit for emitting visible light to the imaging target and a light irradiation operation unit for performing an operation for making the visible light irradiation unit in the light irradiation state; and a controller for controlling operations of the X-ray tube device and the light irradiation device. The controller rotates the anode at an imaging possible rotation speed capable of performing X-ray imaging when the light irradiation operation unit is operated.

10 Claims, 8 Drawing Sheets

X-RAY IMAGING SYSTEM

CROSS-REFERENCE TO RELATED APPLICATIONS

This application claims priority under 35 U.S.C. § 119 to Japanese Patent Application No. 2020-004624 filed on Jan. 15, 2020, the entire disclosure of which is incorporated herein by reference in its entirety.

BACKGROUND OF THE INVENTION

Field of the Invention

The present invention relates to an X-ray imaging system.

Background of the Invention

An X-ray imaging apparatus is known in which X-ray imaging is performed by irradiating a subject with X-rays (see, for example, Patent Document 1). The X-ray imaging apparatus described in Patent Document 1 is provided with an X-ray tube device provided in an imaging room to emit X-rays and an operation console provided in an operating room for controlling the irradiation timing of X-rays to the X-ray tube device. The X-ray tube device has a cathode, an anode, and a rotation drive unit for rotating the anode. The console has an imaging switch capable of being pressed in two stages. The imaging switch instructs the anode to rotate for a predetermined period at a rotation speed required for X-ray imaging by the pressing operation of the first stage and then instructs to perform the X-ray imaging by the pressing operation of the second stage while the anode is rotating. Further, in the X-ray imaging apparatus described in Patent Document 1, a locking switch for pre-rotating the anode is operated before operating the imaging switch.

PRIOR ART DOCUMENT

Patent Document

Patent Document 1: Japanese Unexamined Patent Application Publication No. 2014-191935

SUMMARY OF THE INVENTION

Problems to be Solved by the Invention

In the X-ray imaging apparatus described in Patent Document 1, in order to rotate the anode at the speed required for X-ray imaging, it is required to perform the operation to the locking switch and the imaging switch in this order. Such operations hinder the rapid performance of the X-ray imaging.

Further, in the X-ray imaging apparatus described in Patent Document 1, in some case, after the first stage pressing operation to the imaging switch is performed, the operation of, for example, the adjustment of the irradiation range of the X-rays, the position adjustment of the X-ray tube device and the subject, and the like, may be performed. When time is spent on this operation, a predetermined time has elapsed. As a result, the second stage pressing operation of the imaging switch is not performed, resulting in a stop of the rotation of the anode. In this case, the imaging switch returns to the state where the first stage pressing operation can be performed. When performing X-ray imaging again, the imaging switch needs to be pressed again. As a result, X-ray imaging cannot be performed quickly.

It is an object of the present invention to provide an X-ray imaging system capable of performing X-ray imaging quickly.

Means for Solving the Problem

According to one aspect of the present invention, an X-ray imaging system includes:

an X-ray tube device including a cathode, an anode, and a rotation drive unit for rotating the anode, the X-ray tube device being configured to enable X-ray imaging by emitting electrons generated from the cathode to the anode in a state in which the anode is rotating to irradiate an imaging target with X-rays;

a light irradiation device including a collimator defining an X-ray irradiation range of the X-rays with respect to the imaging target, a visible light irradiation unit for visualizing the X-ray irradiation range by causing a light irradiation state in which visible light is emitted to the imaging target, and a light irradiation operation unit for performing an operation for making the visible light irradiation unit in the light irradiation state; and a controller configured to control operations of the X-ray tube device and the light irradiation device, wherein the controller rotates the anode at an imaging possible rotation speed capable of performing X-ray imaging by the rotation drive unit when the light irradiation operation unit is operated.

Effects of the Invention

According to the present invention, when X-ray imaging is to be performed, it is possible to prevent a state in which rotation of an anode is stopped. With this, for example, it is possible to omit the operation of re-rotating the anode stopped once, which in turn can perform X-ray imaging quickly.

EMBODIMENTS FOR CARRYING OUT THE INVENTION

Hereinafter, an X-ray imaging system of the present invention will be described in detail based on preferred embodiments shown in the accompanying drawings.

Figure 1:
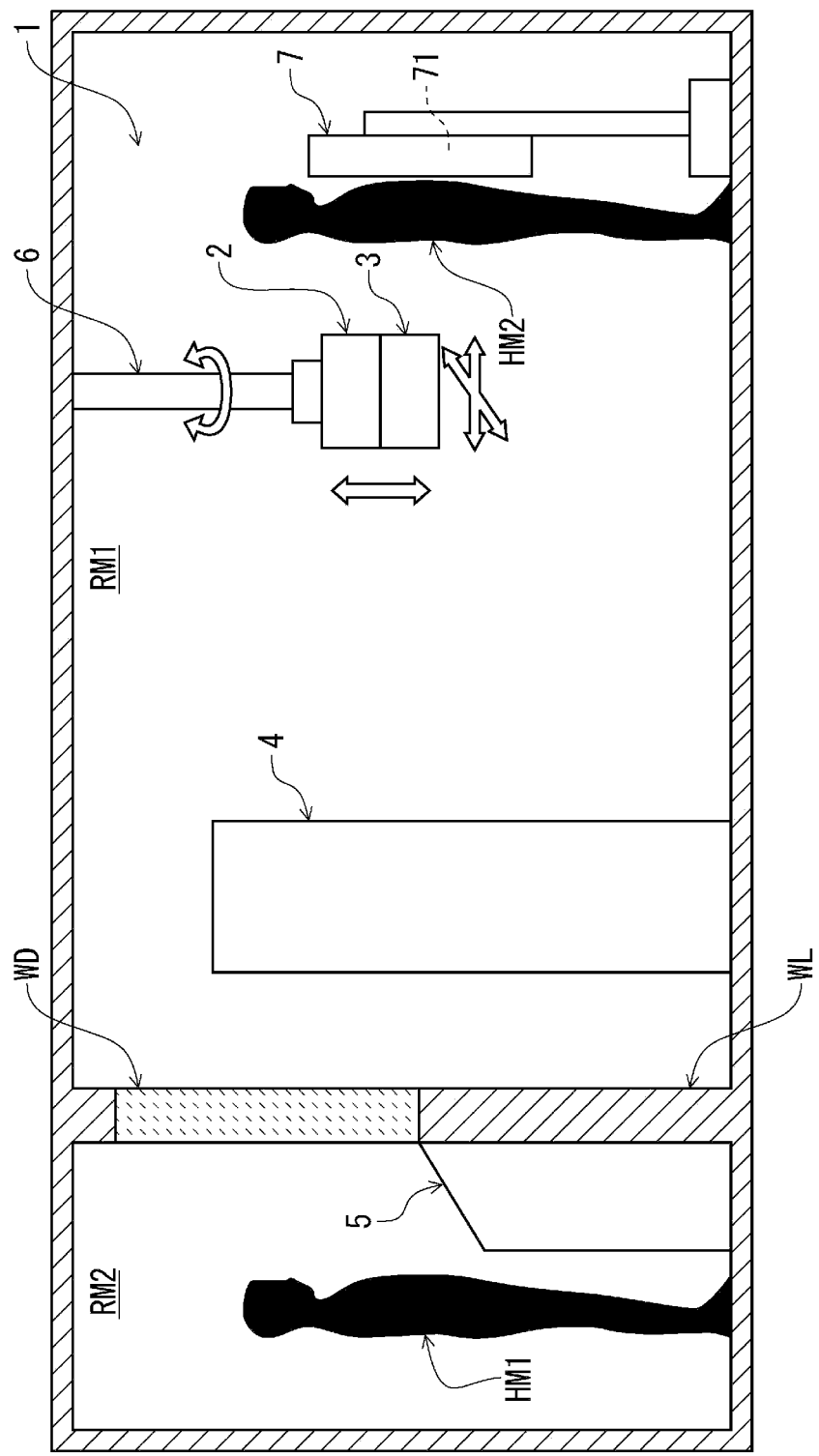
FIG. 1 is a schematic external view of a first embodiment of an X-ray imaging system according to the present invention.
Figure 2:
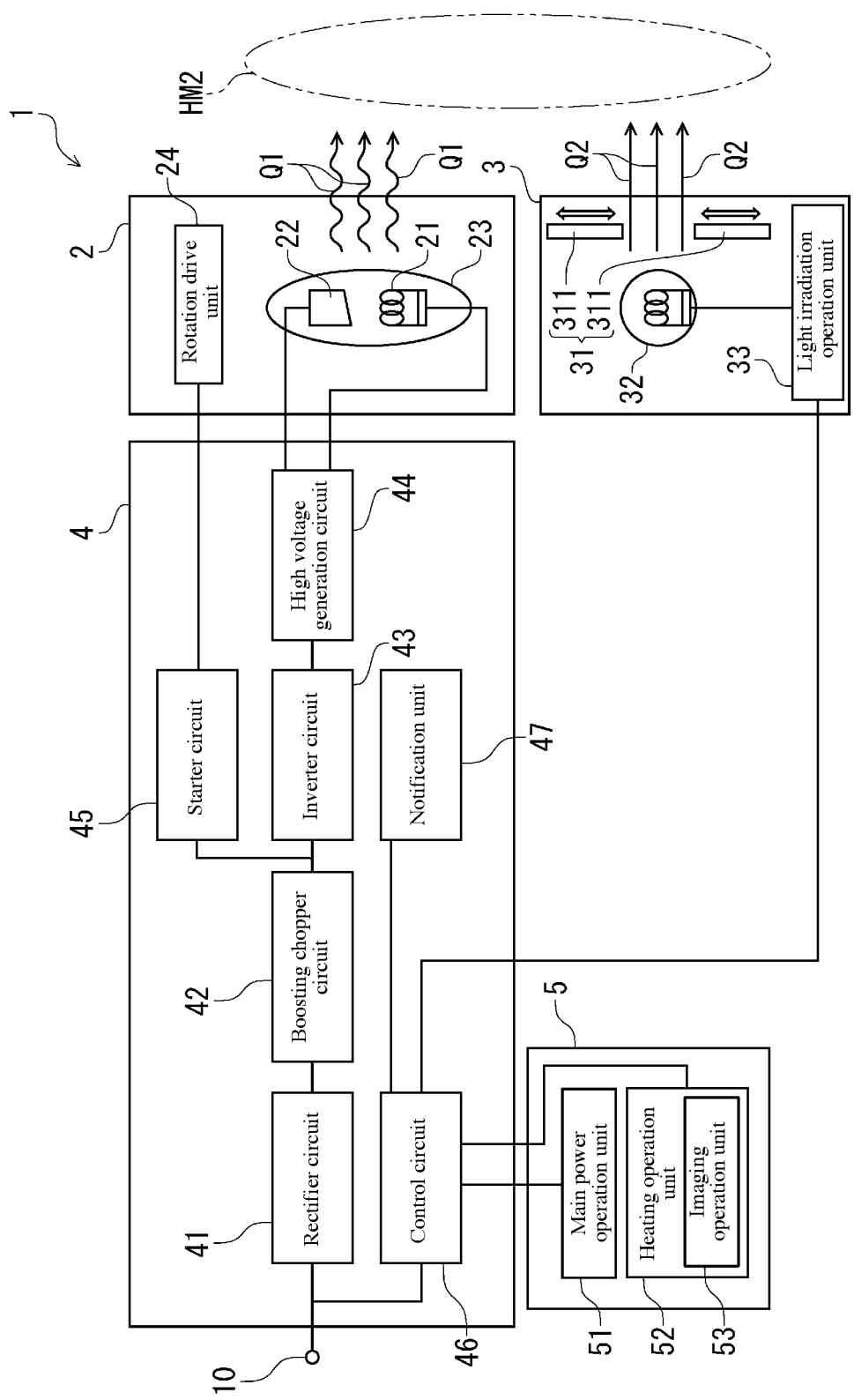
FIG. 2 is a block diagram of the main part of the X-ray imaging system shown in FIG. 1.
Figure 3:
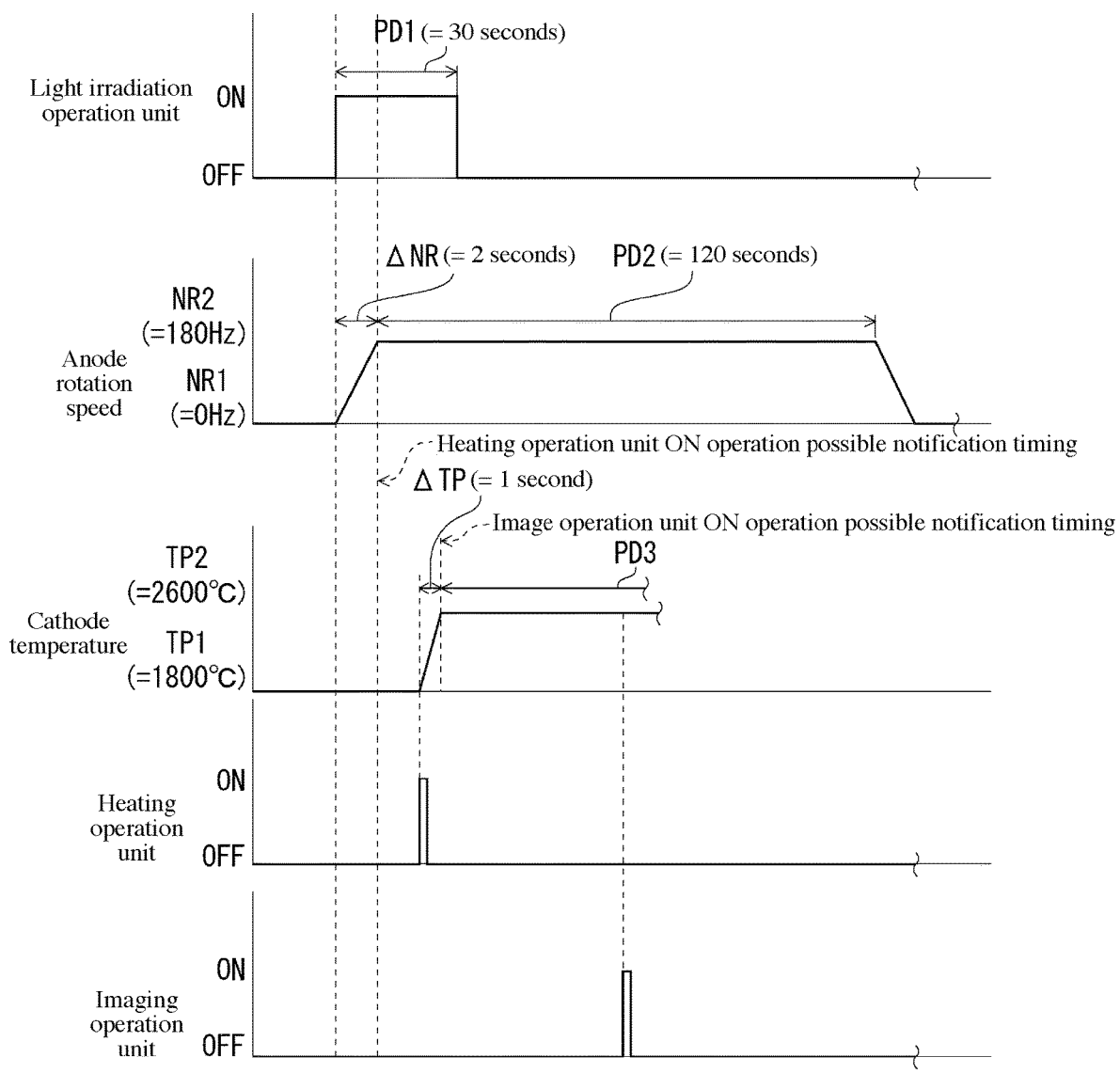
FIG. 3 is a timing chart showing the timings of the operations in the X-ray imaging system shown in FIG. 1.
Figure 4:
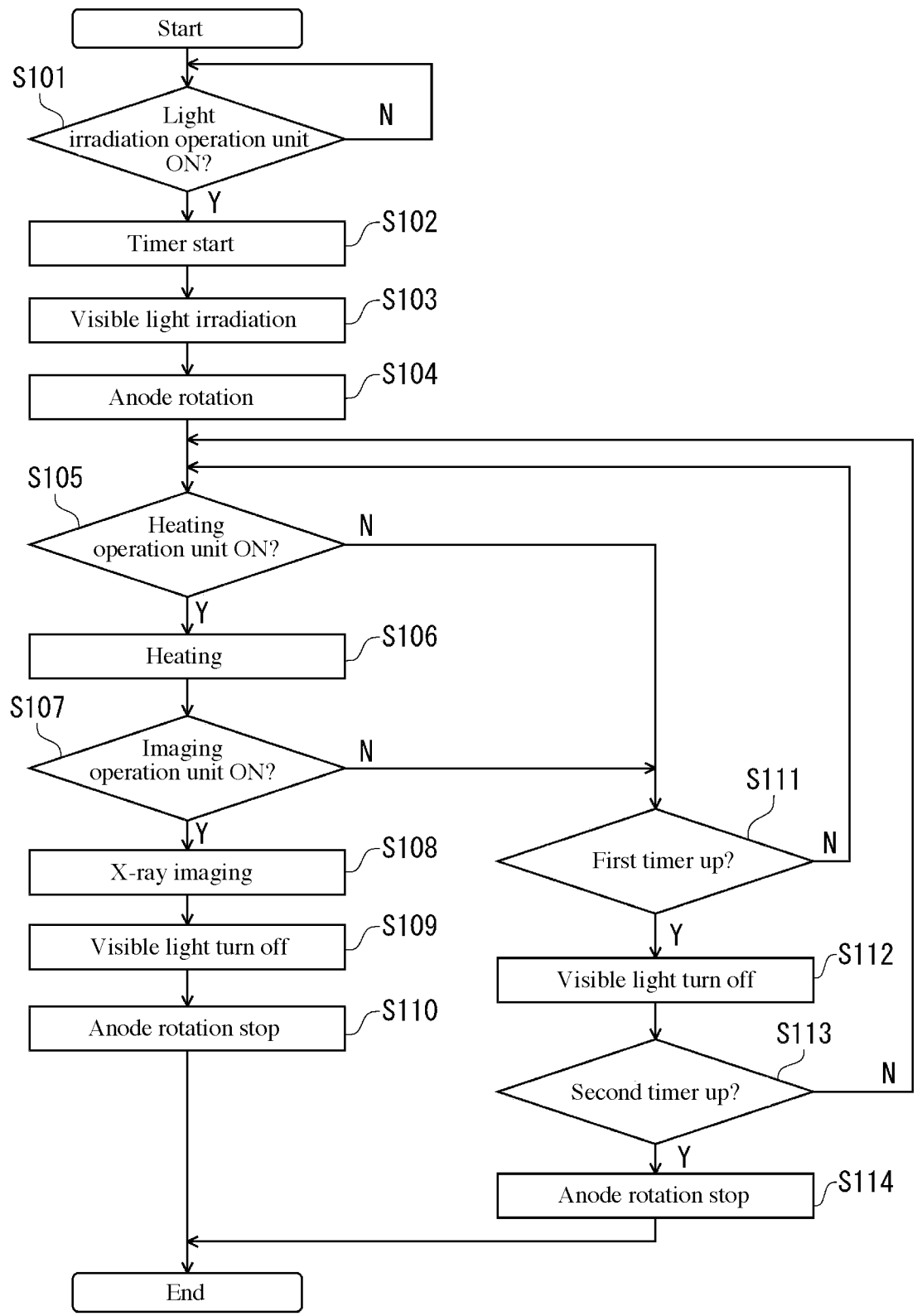
FIG. 4 is a flowchart (one example) showing a control program for performing operations with the timing chart shown in FIG. 3.

FIG. 1 is a schematic external view of a first embodiment of the X-ray imaging system of the present invention. FIG. 2 is a block diagram of the main part of the X-ray imaging system shown in FIG. 1. FIG. 3 is a timing chart showing timings of operations in the X-ray imaging system shown in FIG. 1. FIG. 4 is a flowchart (one example) showing a control program for performing operations with the timing chart shown in FIG. 3. Note that in the following description, for convenience of explanation, the upper side in FIG. 1 is referred to as "upper (or upward)" and the lower side is referred to as "lower (or downward)".

The X-ray imaging system 1 shown in FIG. 1 is a system configured to be capable of X-ray imaging. The X-ray imaging system 1 is provided with an X-ray tube device 2, a light irradiation device (visible light irradiation device) 3, a controller 4, and a main operating device 5, and these devices are electrically connected to each other.

The X-ray tube device 2, the light irradiation device 3, and the controller 4 are arranged in the imaging room RM1. In the imaging room RM1, a support device 6 collectively supporting the X-ray tube device 2 and the light irradiation device 3, and an X-ray imaging table 7 are arranged. The support device 6 and the X-ray imaging table 7 can be a part of the device constituting the X-ray imaging system 1. The main operating device 5 is arranged in an operating room RM2.

Note that the imaging room RM1 and the operating room RM2 are partitioned by a wall WL, and a window WD through which the imaging room RM1 can be seen from the operating room RM2 is provided in the wall WL. A technician HM1, who is an operator of the X-ray imaging system 1, can go in and out of the imaging room RM1 and the operating room RM2. A subject HM2, who is an imaging target, is subjected to X-ray imaging in the imaging room RM1.

Hereinafter, the configuration of each device included in the X-ray imaging system 1 will be described.

As shown in FIG. 2, the X-ray tube device 2 has a cathode (filament) 21, an anode (target) 22, a tube 23, and a rotation drive unit 24.

The cathode 21 and the anode 22 are accommodated in the tube 23 in a state of facing each other. Further, between the cathode 21 and the anode 22, a voltage (tube voltage) of a predetermined magnitude is applied by a high voltage generation circuit 44 of the controller 4.

The rotation drive unit 24 can rotate the anode 22. The subject HM2 can be irradiated with X-rays Q1 when electrons generated from the cathode 21 are emitted to the anode 22 by applying a voltage between the cathode 21 and the anode 22 in a state in which the anode 22 is rotating in the X-ray tube device 2. With this, X-ray imaging to the subject HM2 can be performed. Note that the configuration of the rotation drive unit 24 is not particularly limited. The rotation drive unit 24 may be configured by, for example, a rotor connected to the anode 22 and a stator causing a magnetic field in the rotor to rotate the rotor together with the anode 22.

As shown in FIG. 2, the light irradiation device 3 is provided with a collimator 31, a visible light irradiation unit 32, and a light irradiation operation unit 33.

The collimator 31 can define the X-ray irradiation range of the X-rays Q1 for the subject HM2. The collimator 31 is disposed, for example, between the visible light irradiation unit 32 and the subject HM2 and is provided with a plurality of shutters 311 each made of lead. The collimator 31 is configured to adjust the distance between the shutters 311 by approaching and distancing the shutters 311. Note that the shutters 311 may be manually moved or automatically moved.

The visible light irradiation unit 32 irradiates the subject HM2 with the visible light Q2 in a light irradiation state. The visible light Q2 passes through collimator 31, i.e., passes between the shutters 311 to visualize the X-ray irradiation range on the subject HM2. Note that the visible light irradiation unit 32 is preferably composed of, for example, an LED.

The light irradiation operation unit 33 can be operated to cause the visible light irradiation unit 32 in a light irradiation state. This operation is performed by a technician HM1 in the imaging room RM1. The light irradiation operation unit 33 is preferably configured by, for example, a press operation button switch. The light irradiation operation unit 33 may be configured to turn off the visible light Q2 to release the light irradiation state.

As shown in FIG. 1, the support device 6 is suspended from the ceiling in the imaging room RM1 and is a device for supporting the X-ray tube device 2 and the light irradiation device 3. The support device 6 can collectively move the X-ray tube device 2 and the light irradiation device 3 in the vertical direction and in the horizontal direction and then maintain the stopped state as it is. Further, the support device 6 can collectively rotate the X-ray tube device 2 and the light irradiation device 3 about the vertical axis and then maintain the stopped state as it is. With such a support device 6, the positional relation between the subject HM2 and the X-ray tube device 2 and the light irradiation device 3 can be adjusted in accordance with the size, etc., of the subject HM2. Note that this adjustment is performed by the technician HM1 by gripping and moving, for example, the X-ray tube device 2 in the imaging room RM1.

The X-ray imaging table 7 is provided with a detection unit 71 for detecting X-rays Q1 passed through the subject HM2. The X-rays Q1 from the X-ray tube device 2 pass through the subject HM2 and are detected by the detection unit 71. Thus, an X-ray image is obtained, and X-ray imaging is completed. In this embodiment, the X-ray imaging table 7 is an upright imaging table in which X-ray imaging is performed in a state in which the subject HM2 is in a standing posture. But the present invention is not limited thereto. The X-ray imaging table may be, for example, a bed-type imaging table in which X-ray imaging is performed in a state in which the subject HM2 is in a laying posture.

As shown in FIG. 2, the controller 4 is a device for controlling the operations of the X-ray tube device 2 and the light irradiation device 3. The controller 4 includes a rectifier circuit 41, a boosting chopper circuit 42, an inverter circuit 43, a high voltage generation circuit 44, a starter circuit 45, a control circuit 46, and a notification unit 47.

The rectifier circuit 41 rectifies the AC voltage supplied from the AC power source 10, such as, e.g., a commercial AC power source. In a case where the AC power source 10 is a commercial AC power source, the AC voltage is 200 V.

The boosting chopper circuit 42 boosts the voltage rectified by the rectifier circuit 41. Then, the boosted voltage is applied to the inverter circuit 43 and the starter circuit 45, respectively.

The inverter circuit 43 converts the voltage applied from the boosting chopper circuit 42 to a high-frequency AC output in response to the control signal input from the control circuit 46 and outputs to the high voltage generation circuit 44.

The high voltage generation circuit 44 converts the AC output supplied from the inverter circuit 43 to a DC output and applies between the anode 22 and the cathode 21 of the X-ray tube device 2. Then, as described above, in a state in which the anode 22 is rotating, a voltage is applied between the cathode 21 and the anode 22, so that electrons from the cathode 21 are emitted to the anode 22. Thus, X-rays Q1 are generated.

Further, the high voltage generation circuit 44 can heat the cathode 21 to a predetermined temperature. With this, electrons are generated in the cathode 21. Thus, the high voltage generation circuit 44 functions also as a heating unit for heating the cathode 21. By applying a voltage between the cathode 21 and the anode 22, electrons are moved from the cathode 21 to the anode 22, so that X-rays are emitted.

The starter circuit 45 generates an AC power of two phases of a predetermined voltage and frequency in response to the control signal input from the control circuit 46 and supplies the power to the rotation drive unit 24 of the X-ray tube device 2. This causes the rotation drive unit 24 to be actuated to rotate the anode 22 at a predetermined rotation speed.

The notification unit 47 can notify the state of the X-ray imaging system 1, such as, e.g., that the X-ray imaging system 1 is in a ready-to-use state. The notification method by the notification unit 47 is not particularly limited and may be, for example, a voice method, a light emission method, or a method of combining voice and light emission. Although the notification unit 47 is provided in the controller 4 in this embodiment, the present invention is not limited thereto. The notification unit 47 may be provided in, for example, the main operating device 5.

As shown in FIG. 2, the main operating device 5 is provided with a main power operation unit 51, a heating operation unit 52, and an imaging operation unit 53.

The main power operation unit 51 can perform the operation to activate the X-ray tube device 2, the light irradiation device 3, the controller 4, and the main operating device 5, respectively. The main power operation unit 51 is preferably composed of, for example, a press operation button switch.

The heating operation unit 52 can perform an operation of heating the cathode 21 to an imaging possible temperature TP2 capable of performing X-ray imaging.

The imaging operation unit 53 can perform the operation of causing the X-ray tube device 2 to emit X-rays Q1 to perform X-ray imaging.

The operations for the heating operation unit 52 and the imaging operation unit 53 are performed by the technician HM1 in the operating room RM2.

Further, in this embodiment, the heating operation unit 52 is composed of a press operation button switch configured to be pressed in two stages. In this case, the heating operation unit 52 can heat the cathode 21 to the imaging possible temperature TP2 by the first stage pressing operation and execute X-ray imaging by the second stage pressing operation. Thus, in this X-ray imaging system 1, the heating operation unit 52 has a configuration that also serves as the imaging operation unit 53. Thus, it is possible to prevent the mistake of the operation order of operations to the heating operation unit 52 and the imaging operation unit 53. Therefore, it is possible to accurately perform the respective operations in order. Further, it is possible to quickly perform the continuous operations of the operation to the operation unit 52 and the operation to the imaging operation unit 53. This makes it possible to quickly and smoothly perform the X-ray imaging. Further, it is prevented from constituting the heating operation unit 52 and the imaging operation unit 53 in separate bodies. Therefore, the main operating device 5 can be a simple configuration.

Next, the operation timings of each device in the X-ray imaging system 1 will be described with reference to the timing chart shown in FIG. 3.

First, the X-ray imaging system 1 is in an initial state. Here, the term "initial state" means a state in which the main power operation unit 51 of the main operating device 5 is operated so that the X-ray tube device 2, the light irradiation device 3, the controller 4, and the main operating device 5 are in an operable state, respectively, but the X-rays Q1 and the visible light Q2 are not yet irradiated. As shown in FIG. 3, the initial rotation speed (first rotation speed) NR1 of the anode 22 in the initial state is 0 Hz. Note that the imaging possible rotation speed (second rotation speed) NR2 of the anode 22 at which X-ray imaging becomes available, in other words, the imaging possible rotation speed (second rotation speed) NR2 of the anode 22 required for X-ray imaging is, for example, 180 Hz, in this embodiment, but is not limited thereto. The time ΔNR required from the initial rotation speed NR1 to reach the imaging possible rotation speed NR2 is set to, for example, 2 seconds in this embodiment, but the time ΔNR is not limited thereto.

Further, in the initial state, the cathode 21 is preheated by the high voltage generation circuit 44, and as shown in FIG. 3, the temperature of the cathode 21 is maintained at an initial temperature (first temperature) TP1. Note that the initial temperature TP1 is lower than the imaging possible temperature (second temperature) TP2 at which X-ray imaging can be performed. In this embodiment, for example, the initial temperature TP1 is 1,800° C. and the imaging possible temperature TP2 is 2,600° C., but the present invention is not limited thereto. The time ΔTP from the initial temperature TP1 to the imaging possible temperature TP2 is set to, for example, one second in this embodiment, but the time ΔTP is not limited thereto.

In this initial state, the technician HM1 places the subject HM2 against the X-ray imaging table 7 in the imaging room RM1, and then moves the support device 6 to bring the X-ray tube device 2 and the light irradiation device 3 closer to the position where X-ray imaging to the subject HM2 can be performed.

Then, the technician HM1 operates the light irradiation operation unit 33 of the light irradiation device 3. This operation activates the visible light irradiation unit 32, causing a light irradiation state in which the visible light Q2 is emitted toward the subject HM2. As a result, the technician HM1 can visually recognize the X-ray irradiation range. Note that, as shown in FIG. 3, the irradiation state maintaining period PD1 in which the light irradiation state is maintained is, for example, 30 seconds in this embodiment, but is not limited thereto. The visualization of the X-ray irradiation range is performed during the irradiation state maintaining period PD1.

Further, when the light irradiation operation unit 33 is operated, the visible light irradiation unit 32 is activated, and the rotation drive unit 24 of the X-ray tube device 2 is also activated in accordance with the activation of the visible light irradiation unit 32. With this, as shown in FIG. 3, the anode 22 rotates at the imaging possible rotation speed NR2. The rotation speed maintaining period PD2 in which the imaging possible rotation speed NR2 is maintained is longer than the irradiation state maintaining period PD1, and is, for example, 120 seconds in this embodiment, but is not limited thereto.

Then, as shown in FIG. 3, after the elapse of the time ΔNR from the operation to the light irradiation operation unit 33, it is assumed that the rotation speed has reached the imaging possible rotation speed NR2, and the notification unit 47 of the controller 4 notifies that the operation to the heating operation unit 52 is enabled.

The technician HM1 that has confirmed this notification can move to the operating room RM2 to operate the heating operation unit 52 of the controller 4. By this operation, the cathode 21 is heated to the imaging possible temperature TP2, and the imaging possible temperature TP2 is maintained. The temperature maintaining period PD3 in which the imaging possible temperature TP2 is maintained is preferably longer than the rotation speed maintaining period PD2.

Then, as shown in FIG. 3, after the time TP has elapsed, it is assumed that it has reached the imaging possible temperature TP2, and the notification unit 47 of the controller 4 notifies that it is possible to operate the imaging operation unit 53.

The technician HM1 that has confirmed this notification can operate the imaging operation unit 53 of the controller 4. With this operation, the X-ray imaging is performed.

Note that the confirmation of the X-ray irradiation range when the light irradiation operation unit 33 is operated as described above is generally performed immediately before performing the X-ray imaging. That is, at the time of confirming the X-ray irradiation range, operations, such as, e.g., the adjustment of the X-ray irradiation range and the position adjustment of the X-ray tube device and the subject have been completed, and the remaining operation is to perform the X-ray imaging. Therefore, as long as the anode 22 is rotating at the imaging possible rotation speed NR2 and the cathode 21 has reached the imaging possible temperature TP2, the technician HM1 can perform the X-ray imaging at any timing.

Therefore, in the X-ray imaging system 1, the controller 4 actuates the rotation drive unit 24 in response to the control signal from the control circuit 46 when the light irradiation operation unit 33 is operated. With this operation, the anode 22 can be rotated for the rotation speed maintaining period PD2 at the imaging possible rotation speed NR2. Thus, when attempting to perform X-ray imaging by operating the imaging operation unit 53, it is possible to prevent the state in which the rotation of the anode 22 is stopped. Further, when the rotation speed maintaining period PD2 is 120 seconds, it is considered that the imaging operation unit 53 can be reliably operated in the rotation speed maintaining period PD2.

When operating the operating imaging operation unit 53, the technician HM1 can perform the operation to the imaging operation unit 53 at any timing by waiting for the time ΔTP after operating the heating operation unit 52 within the rotation speed maintaining period PD2 without paying attention to whether or not the anode 22 is rotating.

Through the above-described operations, X-ray imaging can be performed quickly and smoothly.

Further, in the X-ray imaging system 1, it is possible to omit the operation of re-rotating the anode 22 whose rotation is once stopped, which operation occurs in the X-ray imaging apparatus described in the above-described Patent Document 1, and therefore, faster X-ray imaging can be performed.

As shown in FIG. 3, the control circuit 46 of the controller 4 sets the rotation speed maintaining period PD2 longer than the irradiation state maintaining period PD1. As a result, it is possible to secure the time required to confirm the X-ray irradiation range within the irradiation state maintaining period PD1 neither too much nor too little. Further, within the rotation speed maintaining period PD2, it is possible to secure the time required for the technician HM1 to move from the imaging room RM1 to the operating room RM2 and the time required to operate the heating operation unit 52 and the imaging operation unit 53 neither too much nor too little.

The control circuit 46 of the controller 4 has an interlock function that enables the operation to the heating operation unit 52 when the light irradiation operation unit 33 is operated. This restricts the operation to the heating operation unit 52 until the light irradiation operation unit 33 is operated. Therefore, the operation can be accurately performed in the operation order of operating the light irradiation operation unit 33 and then operating the heating operation unit 52.

Further, as described above, the notification unit 47 can notify that the operation to the heating operation unit 52 can be performed and the operation to the imaging operation unit 53 can be performed. With this, it is possible to prevent an erroneous operation to perform the operation to the heating operation unit 52 before the operation enables. In the same manner, it is possible to prevent an erroneous operation to perform the operation to the imaging operation unit 53 before the operation enables. Note that it is enough that the notification unit 47 can notify at least one of these notifications.

Further, as described above, in the X-ray imaging apparatus described in Patent Document 1, it is configured such that "after performing the operation of preliminarily rotating the anode, the operation of rotating the anode at the rotation speed required for X-ray imaging is performed", that is, "in order to rotate the anode at the rotation speed required for X-ray imaging, two operations are required". In contrast, in the X-ray imaging system 1, by simply operating the light irradiation operation unit 33 once, it is possible to rotate the anode 22 at the imaging possible rotation speed NR2 required for X-ray imaging. Such a configuration makes it possible to suppress the number of operations, which in turn can contribute to quick X-ray imaging.

Further, it is also possible to shorten the rotation speed maintaining period PD2 during which the imaging possible rotation speed NR2 is maintained as much as possible. Thus, it is possible to suppress or prevent the shortening of the life of the rotation drive unit 24 for rotating the anode 22.

Next, an example of the control program for performing operations according to the timing chart shown in FIG. 3 will be described with reference to the flowchart shown in FIG. 4. Note that this control program is stored in advance, for example, in the storage circuit (not shown) of the controller 4.

First, when the light irradiation operation unit 33 is operated (Step S101), a timer (not shown) built-in the controller 4 is operated (Step S102). In accordance with the timer operation, the visible light Q2 is emitted by the visible light irradiation unit 32 (Step S103), and the anode 22 is rotated at the imaging possible rotation speed NR2 by the rotation drive unit 24 (Step S104). Note that the order of Step S103 and Step S104 may be interchanged.

Next, it is determined whether or not the heating operation unit 52 has been operated (Step S105). As a result of the determination in Step S105, when it is determined that the heating operation unit 52 has been operated, the cathode 21 is heated to the imaging possible temperature TP2 by the high voltage generation circuit 44 (Step S106).

Next, it is determined whether or not the imaging operation unit 53 has been operated (Step S107). When it is determined that the imaging operation unit 53 has been operated as a result of the determination in Step S107, X-ray imaging is performed (Step S108). The operation to the visible light irradiation unit 32 is stopped to turn off the visible light Q2 (Step S109), and the operation to the rotation drive unit 24 is stopped to stop the rotation of the anode 22 (Step S110). The order of Step S109 and Step S110 may be interchanged.

As a result of the determination in Step S105, when it is determined that the heating operation unit 52 has not been operated, it is determined whether or not the irradiation state maintaining period PD1 has elapsed (first time-up) (Step S111). Then, as a result of the determination in Step S111, when it is determined that the irradiation state maintaining period PD1 has elapsed, the operation to the visible light irradiation unit 32 is stopped to turn off the visible light Q2 (Step S112). On the other hand, as a result of the determination in Step S111, when it is determined that the irradiation state maintaining period PD1 has not passed, the process returns to Step S105 and performs the subsequent steps one by one.

Following the execution in Step S112, it is determined whether or not the rotation speed maintaining period PD2 has elapsed (second time-up) (Step S113). Then, as a result of the determination in Step S113, when it is determined that the rotation speed maintaining period PD2 has elapsed, the operation to the rotation drive unit 24 is stopped, the rotation of the anode 22 is stopped (Step S114). On the other hand, as a result of the determination in Step S113, when it is determined that the rotation speed maintaining period PD2 has not elapsed, the process returns to Step S105, and the subsequent Steps are sequentially executed.

Further, as a result of the determination in Step S107, when it is determined that the imaging operation unit 53 has not been operated, Step S111 and subsequent steps are sequentially performed.

With the above-described control program, the X-ray imaging system 1 can be operated with the timing chart shown in FIG. 3.

Second Embodiment

Figure 5:
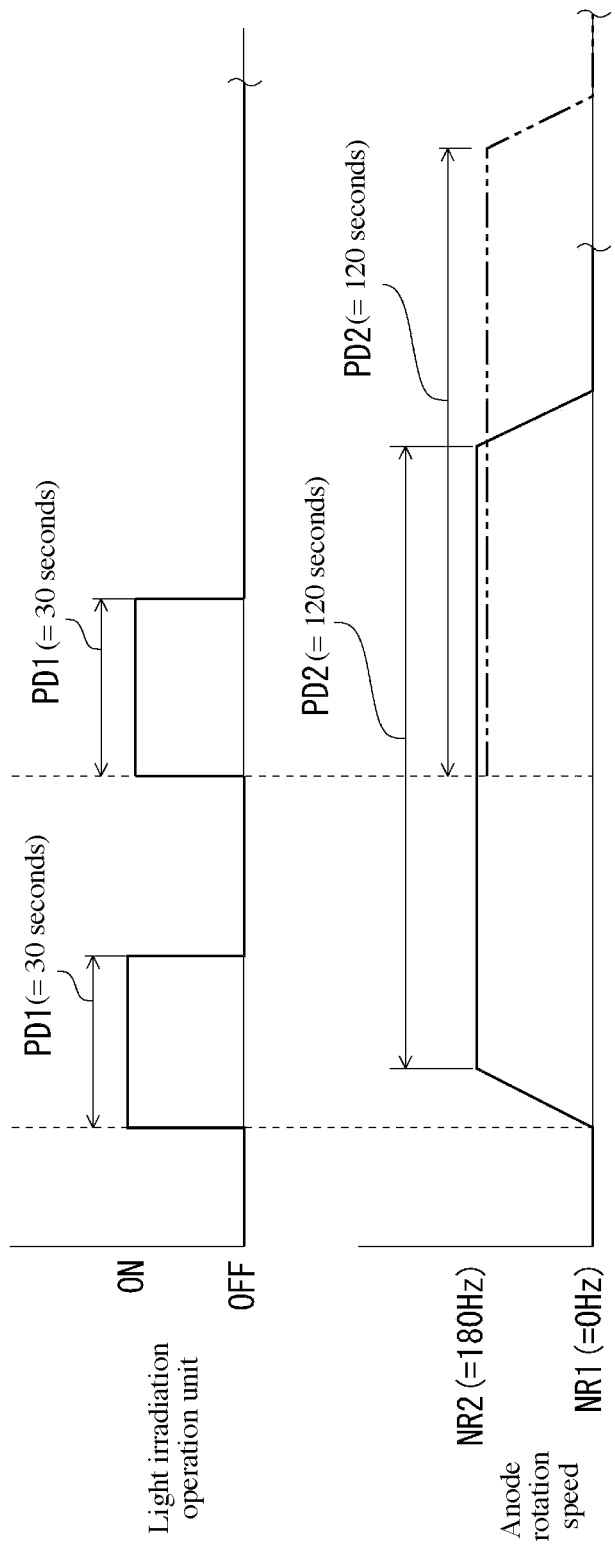
FIG. 5 is a timing chart showing the timings of operations in the X-ray imaging system (second embodiment) of the present invention.
Figure 6:
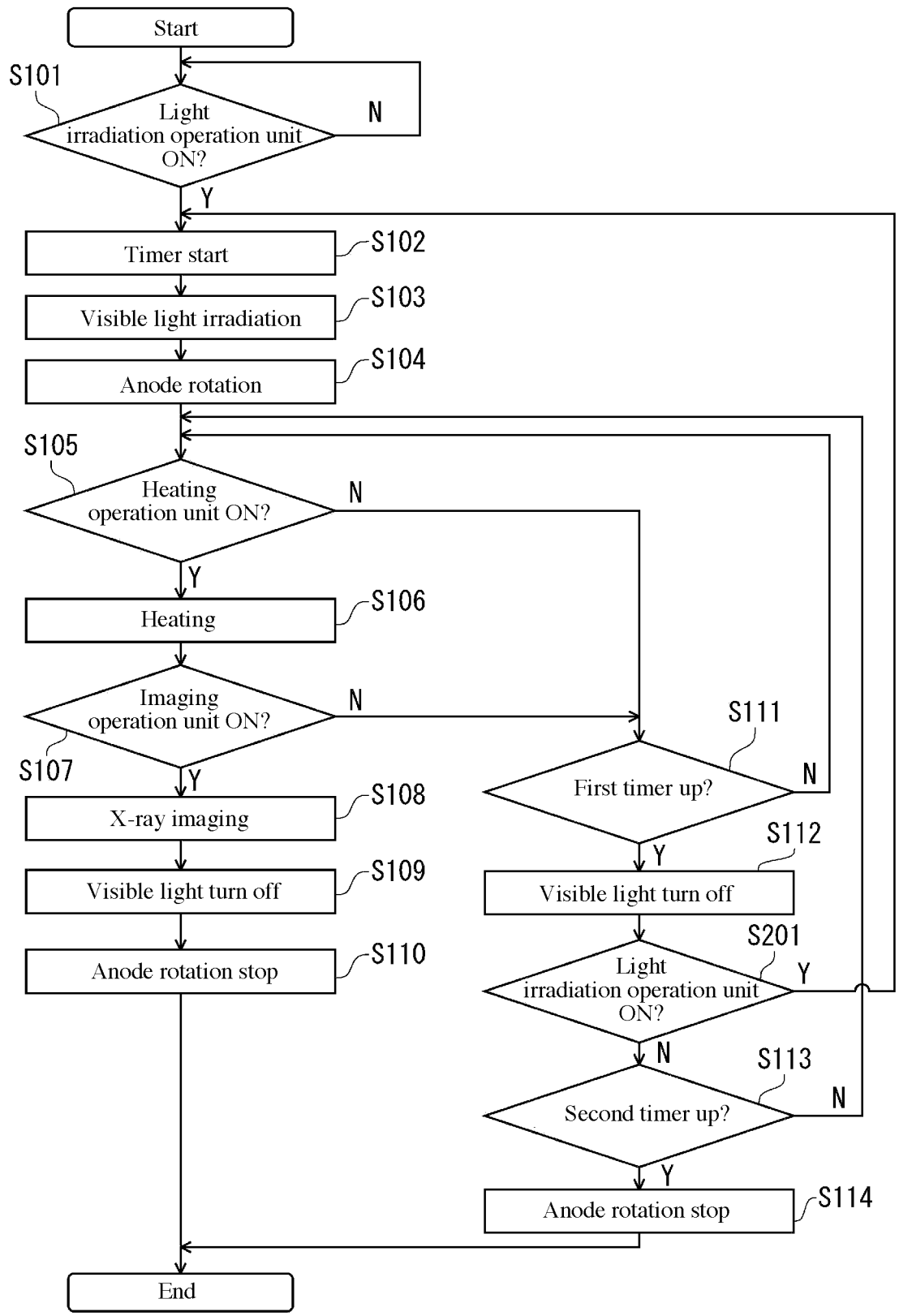
FIG. 6 is a flowchart (one example) showing a control program for performing operations with the timing chart shown in FIG. 5.

FIG. 5 is a timing chart showing the timings of operations in an X-ray imaging system (second embodiment) of the present invention. FIG. 6 is a flowchart showing a control program for performing operations with the timing chart shown in FIG. 5.

Hereinafter, referring to these drawings, the second embodiment of the X-ray imaging system of the present invention will be described below, but the differences from the above-described embodiment will be mainly described, and descriptions of the same items will be omitted.

This embodiment is the same as the first embodiment except that the timing chart differs.

As shown in FIG. 5, in this embodiment, when the light irradiation operation unit 33 is operated again between the end of the irradiation state maintaining period PD1 and the end of the rotation speed maintaining period PD2, the rotation speed maintaining period PD2 is restarted, that is, the rotation speed maintaining period PD2 is reset. With this, the rotation speed maintaining period PD2 is continuously maintained from the time of the re-operation to the light irradiation operation unit 33. This control is performed by the controller 4.

For example, there is a case in which a technician HM1 is away from the X-ray imaging system 1 due to various circumstances after performing the first operation to the light irradiation operation unit 33. In this case, even within the rotation speed maintaining period PD2, the light irradiation operation unit 33 is operated again to reconfirm the X-ray irradiation range to the subject HM2, instead of operating the heating operation unit 52 and the imaging operation unit 53 as they are.

Therefore, in the X-ray imaging system 1, even in a case where the technician HM1 is once separated from the X-ray imaging system 1, it is configured such that the anode 22 is continuously rotated each time the light irradiation operation unit 33 is re-operated, so that the operation with the timing chart shown in FIG. 5 is enabled. With this, the technician HM1 can operate the imaging operation unit 53 without paying attention to whether or not the anode 22 is rotating.

Next, referring to the flowchart shown in FIG. 6, an example of a control program for executing an operating with the timing chart shown in FIG. 5 will be described.

As shown in FIG. 6, in the control program, Step S201 is executed between Step S112 and Step S113. Step S201 is a step for determining whether or not the light irradiation operation unit 33 has been operated.

As a result of the determination in Step S201, when it is determined that the light irradiation operation unit 33 has been operated, the process returns to Step S102, and the subsequent steps will be sequentially executed. On the other hand, as a result of the determination in Step S201, when it is determined that the light irradiation operation unit 33 has not been operated, Step S113 and the subsequent steps will be sequentially executed.

With the above-described control program, the X-ray imaging system 1 can be operated with the timing chart shown in FIG. 5.

Third Embodiment

Figure 7:
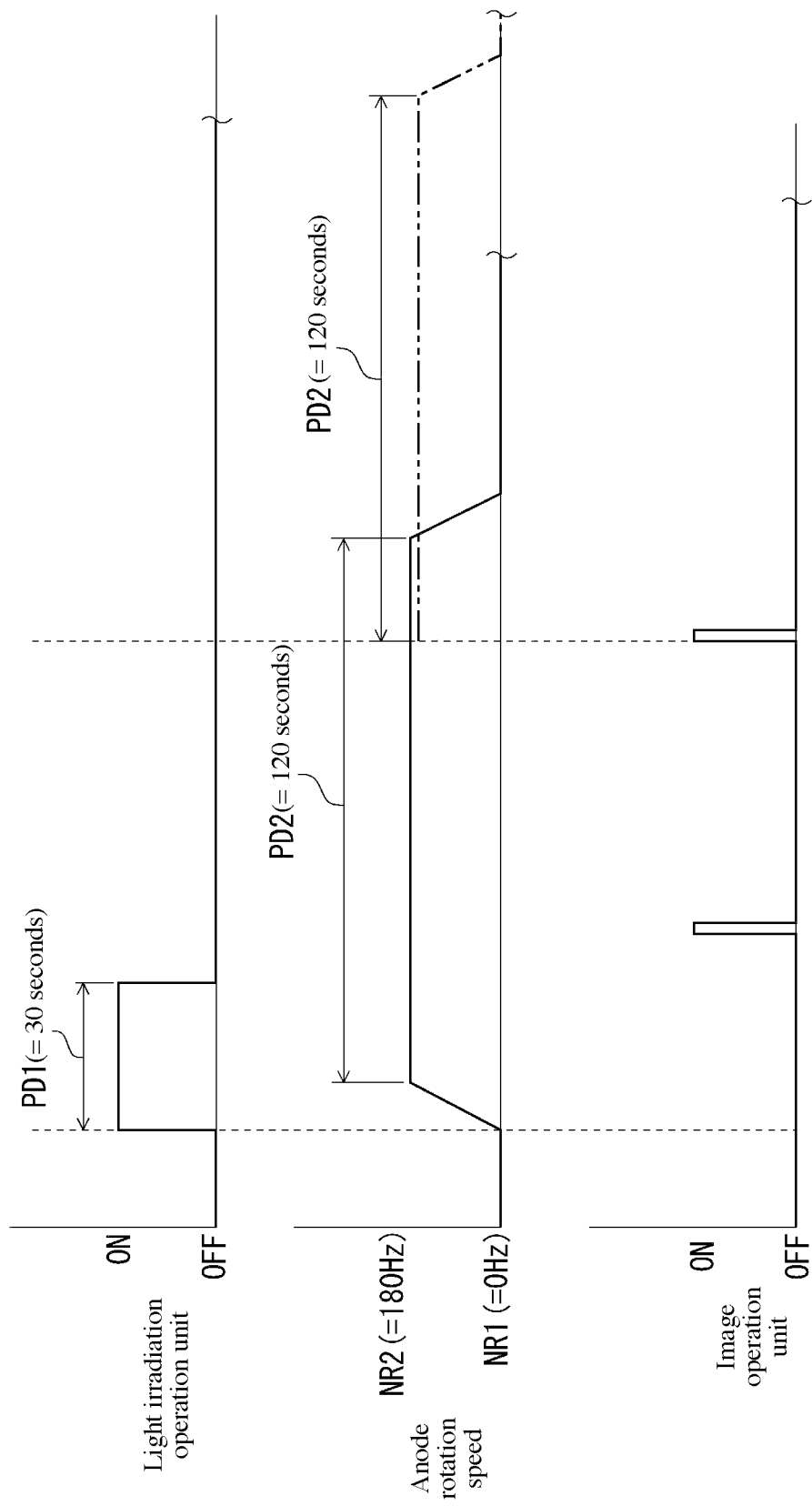
FIG. 7 is a timing chart showing the timings of operations in the X-ray imaging system (third embodiment) of the present invention.
Figure 8:
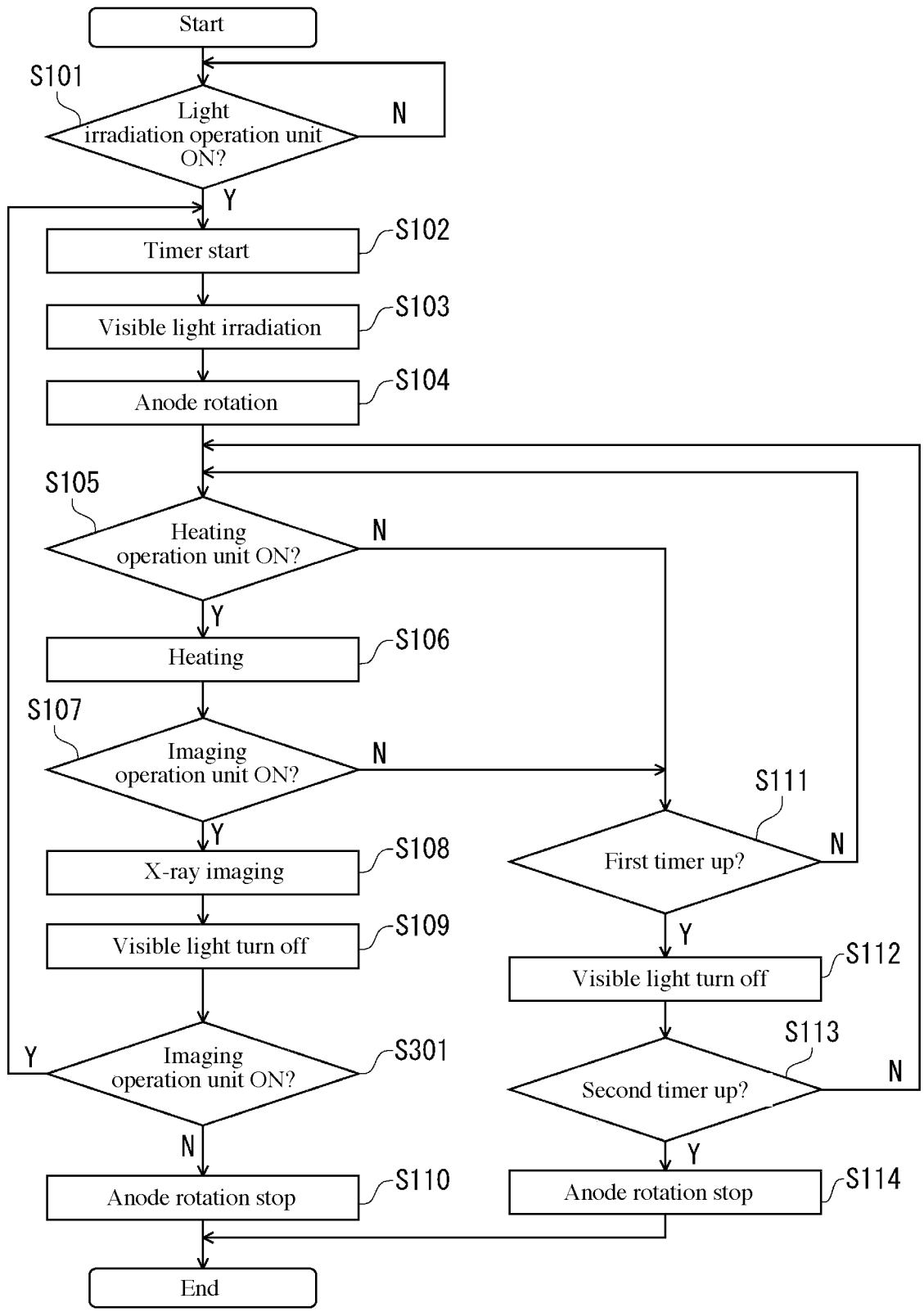
FIG. 8 is a flowchart (one example) showing a control program for performing operations with the timing chart shown in FIG. 7.

FIG. 7 is a timing chart showing the timings of operations in an X-ray imaging system (third embodiment) of the present invention. FIG. 8 is a flowchart showing a control program for performing operations with the timing chart shown in FIG. 7.

Hereinafter, referring to these drawings, the third embodiment of the X-ray imaging system of the present invention will be described, but the differences from the embodiments described above will be mainly described, and the descriptions of the same items will be omitted.

This embodiment is the same as the first embodiment except that the timing chart differs.

As shown in FIG. 7, in this embodiment, between the end of the irradiation state maintaining period PD1 and the end of the rotation speed maintaining period PD2, when the imaging operation unit 53 is operated and the imaging operation unit 53 is further operated, the rotation speed maintaining period PD2 is restarted, that is, the rotation speed maintaining period PD2 is reset. This control is performed by the controller 4.

For example, there is a case in which after performing the X-ray imaging of the subject HM2, for the purpose of performing X-ray imaging of the subject HM2 again, the subject HM2 is not replaced with a next scheduled subject HM2.

Therefore, in the X-ray imaging system 1, it is configured such that after the X-ray imaging, in order that the rotation of the anode 22 is continued every time the imaging operation unit 53 is operated again, it is configured that the operations with the timing chart shown in FIG. 7 can be performed. With this, the technician HM1 can operate the imaging operation unit 53 without paying attention to whether or not the anode 22 is rotating.

Note that the resetting of the rotation speed maintaining period PD2 may be performed when the imaging operation unit 53 is operated and the light irradiation operation unit 33 is further operated before performing the imaging operation unit 53.

Next, referring to the flowchart shown in FIG. 8, an example of the control program for executing the operations with the timing chart shown in FIG. 7 will be described.

As shown in FIG. 8, in the control program, Step S301 is executed between Step S109 and Step S110. Step S301 is a step for determining whether or not the imaging operation unit 53 has been operated.

As a result of the determination in Step S301, when it is determined that the imaging operation unit 53 has been operated, the process returns to Step S102, and the subsequent steps will be sequentially executed. On the other hand, as a result of the determination in Step S301, when it is determined that the imaging operation unit 53 has not been operated, Step S110 and the subsequent steps will be sequentially executed.

With the above-described control program, the X-ray imaging system 1 can be operated with the timing chart shown in FIG. 7.

Although the X-ray imaging system of the present invention has been described with reference to the illustrated embodiments, the present invention is not limited thereto, and each part constituting the X-ray imaging system can be replaced with any configuration capable of performing a similar function. An optional component may also be added.

Further, in the X-ray imaging system 1, the initial rotation speed NR1 and the imaging possible rotation speed NR2 may be arbitrarily set.

Further, in the X-ray imaging system 1, the initial temperature TP1 and the imaging possible temperature TP2 may be arbitrarily set.

Further, in the X-ray imaging system 1, the lengths of irradiation state maintaining period PD1, rotation speed maintaining period PD2, and temperature maintaining period PD3 can be arbitrarily set.

Further, in the X-ray imaging system 1, as shown in FIG. 3, the anode 22 rotating at 180 Hz is stopped, that is, the rotation speed is reduced to 0 Hz, but the rotation speed is not limited to this, and the rotation speed may be reduced to a level not reaching 0 Hz, for example, 60 Hz.

[Aspects]

It will be understood by those skilled in the art that the plurality of exemplary embodiments described above is illustrative of the following aspects.

(Item 1)

An X-ray imaging system according to one aspect of the present invention includes:

an X-ray tube device including a cathode, an anode, and a rotation drive unit for rotating the anode, the X-ray tube device being configured to enable X-ray imaging by emitting electrons generated from the cathode to the anode in a state in which the anode is rotating to irradiate an imaging target with X-rays;

a light irradiation device including a collimator defining an X-ray irradiation range of the X-rays with respect to the imaging target, a visible light irradiation unit for visualizing the X-ray irradiation range by causing a light irradiation state in which visible light is emitted to the imaging target, and a light irradiation operation unit for performing an operation for making the visible light irradiation unit in the light irradiation state; and a controller configured to control operations of the X-ray tube device and the light irradiation device, wherein the controller rotates the anode at an imaging possible rotation speed capable of performing X-ray imaging by the rotation drive unit when the light irradiation operation unit is operated.

According to the X-ray imaging system described in the above-described Item 1, when X-ray imaging is to be performed, it is possible to prevent the state in which the rotation of the anode is stopped. With this, for example, it is possible to omit the operation for re-rotating the once-stepped anode, which in turn can perform quick X-ray imaging.

(Item 2)

In the X-ray imaging system as recited in the above-described Item 1, the controller sets a rotation speed maintaining period during which the imaging possible rotation speed is maintained to be longer than an irradiation state maintaining period during which the light irradiation state is maintained.

According to the X-ray imaging system described in Item 2, for example, within the irradiation state maintaining period, the time required for checking the X-ray irradiation range can be ensured neither too much nor too little. Further, within the rotation speed maintaining period, for example, it is possible to secure the time required for moving a technician from the imaging room to the operating room or for operating the heating operation unit and the imaging operation unit neither too much nor too little.

(Item 3)

In the X-ray imaging system as recited in the above-described Item 2, the controller restarts the rotation speed maintaining period when the light irradiation operation unit is operated between an end of the irradiation state maintaining period and an end of the rotation speed maintaining period.

According to the X-ray imaging system as recited in the above-described Item 3, for example, even when the technician is away from the X-ray imaging system once, the rotation of the anode is continuously performed every time the light irradiation operation unit is re-operated. Thus, the technician can perform X-ray imaging without paying attention to whether or not the anode is rotating.

(Item 4)

In the X-ray imaging system as recited in any one of the above-described Items 1 to 3, the X-ray tube device includes a heating unit for heating the cathode.

According to the X-ray imaging system as recited in the above-described Item 4, it is possible to promote the generation of electrons in the cathode.

(Item 5)

The X-ray imaging system as recited in the above-described Item 4, further including:

a main operating device including a heating operation unit for performing an operation to the heating unit to heat the cathode to an imaging possible temperature capable of performing the X-ray imaging.

According to the X-ray imaging system as recited in the above-described Item 5, for example, the main operating device can be arranged in a separate room by separating from the X-ray tube device, the light irradiation device, and the controller.

(Item 6)

In the X-ray imaging system as recited in the above-described Item 5, the main operating device includes an imaging operation unit for causing the X-ray tube device to perform the X-ray imaging.

According to the X-ray imaging system as recited in the above-described Item 6, the operation to the imaging operation unit can be performed in a separate room.

(Item 7)

In the X-ray imaging system as recited in the above-described Item 6, the controller restarts the rotation speed maintaining period in a case where one of the light irradiation operation unit and the imaging operation unit is operated before the other operation unit during a period between an end of the irradiation state maintaining period and an end of the rotation speed maintaining period.

According to the X-ray imaging system as recited in the above-described Item 7, after performing X-ray imaging, the rotation of the anode is continuously performed each time the imaging operation unit is operated again. Thus, the technician can perform X-ray imaging without paying attention to whether or not the anode is rotating.

(Item 8)

In the X-ray imaging system as recited in the above-described Item 6 or 7, the heating operation unit serves also as the imaging operation unit.

According to the X-ray imaging system as recited in the above-described Item 8, the operation to the heating operation unit and the operation to the imaging operation unit can be performed accurately in order.

(Item 9)

In the X-ray imaging system as recited in any one of the above-described Items 5 to 8, the controller enables an operation to the heating operation unit when the light irradiation operation unit is operated.

According to the X-ray imaging system as recited in the above-described Item 9, until the light irradiation operation unit is operated, the operation to the heating operation unit is regulated, and therefore the operation can be accurately performed in the operation order of operating on the light irradiation operation unit and then operating on the heating operation unit.

(Item 10)

In the X-ray imaging system as recited as recited in any one of the above-described Items 6 to 8, the controller includes a notification unit for notifying at least one of an indication that an operation to the heating operation unit is enabled and an indication that an operation to the imaging operation unit is enabled.

According to the X-ray imaging system as recited in the above-described Item 10, it is possible to prevent an erroneous operation of performing the operation to the heating operation unit before the operation becomes enabled. Further, it is possible to prevent an erroneous operation to perform the operation to the imaging operation unit before the operation becomes enabled.

DESCRIPTION OF SYMBOLS

1: X-ray imaging system
2: X-ray tube device
  21: Cathode (filament)
  22: Anode (target)
  23: X ray tube
  24: Rotation drive unit
3: Light irradiation device (visible light irradiation device)
  31: Collimator
    311: Shutter
  32: Visible light irradiation unit
  33: Light irradiation operation unit
4: Controller
  41: Rectifier circuit
  42: Boosting chopper circuit
  43: Inverter circuit
  44: High voltage generation circuit
  45: Starter circuit
  46: Control circuit
  47: Notification unit
5: Main operating device
  51: Main power operation unit
  52: Heating operation unit
  53: Imaging operation unit
6: Support device
7: X-ray imaging table
  71: Detection unit
10; AC power source
HM1: Technician
HM2: Subject
NR1: Initial rotation speed (first rotation speed)
NR2: Imaging possible rotation speed (second rotation speed)
PD1: Irradiation state maintaining period
PD2: Rotation speed maintaining period
PD3: Temperature maintaining period
Q1: X-ray
Q2: Visible light
RM1: Imaging room
RM2: Operating room
S101 to S114, S201, S301: Step
TP1: Initial temperature (first temperature)
TP2: Imaging possible temperature (second temperature)
ΔTP, ΔNR: Time
WD: Window
WL: Wall

The invention claimed is:

1. An X-ray imaging system comprising:
an X-ray tube device including a cathode, an anode, and a rotation drive unit for rotating the anode, the X-ray tube device being configured to enable X-ray imaging by emitting electrons generated from the cathode to the anode in a state in which the anode is rotating to irradiate an imaging target with X-rays;
a light irradiation device including a collimator defining an X-ray irradiation range of the X-rays with respect to the imaging target, a visible light irradiation unit for visualizing the X-ray irradiation range by causing a light irradiation state in which visible light is emitted to the imaging target, and a light irradiation operation unit for performing an operation for making the visible light irradiation unit in the light irradiation state; and
a controller configured to control operations of the X-ray tube device and the light irradiation device,
wherein the controller rotates the anode at an imaging possible rotation speed capable of performing X-ray imaging by the rotation drive unit when the light irradiation operation unit is operated.

2. The X-ray imaging system as recited in claim 1,
wherein the controller sets a rotation speed maintaining period during which the imaging possible rotation speed is maintained to be longer than an irradiation state maintaining period during which the light irradiation state is maintained.

3. The X-ray imaging system as recited in claim 2,
wherein the controller restarts the rotation speed maintaining period when the light irradiation operation unit is operated between an end of the irradiation state maintaining period and an end of the rotation speed maintaining period.

4. The X-ray imaging system as recited in claim 1,
wherein the X-ray tube device includes a heating unit for heating the cathode.

5. The X-ray imaging system as recited in claim 4, further comprising:
a main operating device including a heating operation unit for performing an operation to the heating unit to heat the cathode to an imaging possible temperature capable of performing the X-ray imaging.

6. The X-ray imaging system as recited in claim 5,
wherein the controller enables an operation to the heating operation unit when the light irradiation operation unit is operated.

7. The X-ray imaging system as recited in claim 5,
wherein the main operating device includes an imaging operation unit for causing the X-ray tube device to perform the X-ray imaging.

8. The X-ray imaging system as recited in claim 7,
wherein the controller sets a rotation speed maintaining period during which the imaging possible rotation speed is maintained to be longer than an irradiation state maintaining period during which the light irradiation state is maintained;
wherein the controller restarts the rotation speed maintaining period in a case where one of the light irradiation operation unit and the imaging operation unit is operated before the other operation unit during a period between an end of the irradiation state maintaining period and an end of the rotation speed maintaining period.

9. The X-ray imaging system as recited in claim 7,
wherein the heating operation unit serves also as the imaging operation unit.

10. The X-ray imaging system as recited in claim 7,
wherein the controller includes a notification unit for notifying at least one of an indication that an operation to the heating operation unit is enabled and an indication that an operation to the imaging operation unit is enabled.

* * * * *